US006221385B1

United States Patent
Camu et al.

(10) Patent No.: US 6,221,385 B1
(45) Date of Patent: Apr. 24, 2001

(54) FREEZE DRIED LIPOSOME ENCAPSULATED AMPHIPHILIC DRUG COMPOSITIONS AND A PROCESS FOR THE PREPARATION THEREOF

(75) Inventors: Frederic Camu, Nieuwrkerken; Robert Brasseur, Haillot; Franz Legros, Jumet; Sandra Carlino, Tubize, all of (BE)

(73) Assignee: Vrije Universiteit Brussel, Brussels (BE)

( * ) Notice: Subject to any disclaimer, the term of this patent is extended or adjusted under 35 U.S.C. 154(b) by 0 days.

(21) Appl. No.: 09/147,254

(22) PCT Filed: May 12, 1997

(86) PCT No.: PCT/EP97/02421

§ 371 Date: Feb. 2, 1999

§ 102(e) Date: Feb. 2, 1999

(87) PCT Pub. No.: WO97/42936

PCT Pub. Date: Nov. 20, 1997

(30) Foreign Application Priority Data

May 10, 1996 (GB) .................................................. 9609779

(51) Int. Cl.[7] .................................................. A61K 9/127

(52) U.S. Cl. .............................. 424/450; 264/4.1; 264/4.3
(58) Field of Search .............................. 424/450; 264/4.1, 264/4.3

(56) References Cited

FOREIGN PATENT DOCUMENTS

| 41 24 252 | 1/1993 | (DE) . |
|---|---|---|
| 0021337 A2 | 1/1981 | (EP) . |
| 0 317 120 | 4/1989 | (EP) . |
| 2 592 791 | 7/1987 | (FR) . |
| 2 256 139 | 12/1992 | (GB) . |
| 87 01933 | 4/1987 | (WO) . |
| WO93/00807 | 1/1993 | (WO) . |

OTHER PUBLICATIONS

Chemical Abstract 116:181024 & Chem. Pharm. Bull. (40(1), pp. 1–5 (1992) (see abstract).

Primary Examiner—Gollamudi S. Kishore
(74) Attorney, Agent, or Firm—Bacon & Thomas

(57) ABSTRACT

A process for the preparation of freeze dried liposome encapsulated amphiphilic drug compositions, which process comprises preparing a liposomal suspension of multilamellar vesicles (MLVs) which encapsulate an amphiphilic drug compsition, adding sorbitol to the liposomal suspension and lyophilisation of the suspension.

11 Claims, 1 Drawing Sheet

Laser Light Scattering curve plotting log of the vesicle diameter against percentage of the total number of vesicles before and after freeze-drying and rehydration.

Laser Light Scattering curve plotting log of the vesicle diameter against percentage of the total number of vesicles before and after freeze-drying and rehydration.

FREEZE DRIED LIPOSOME ENCAPSULATED AMPHIPHILIC DRUG COMPOSITIONS AND A PROCESS FOR THE PREPARATION THEREOF

This application is a 371 of PCT/EP97/02421 filed May 12, 1997.

The present invention relates to freeze dried liposome encapsulated drug compositions and to a process for the preparation thereof. In particular, the present invention relates to freeze dried liposome/bupivacaine compositions.

The major problems which are encountered during liposome drug storage in vesicular suspensions are the chemical alterations of the liposome compounds, particularly, phospholipids leading to toxic degradation products, the leakage of the drug from the liposomes and the modifications of the size and the morphology of the phospholipid liposome vesicles through aggregation, fusion and size increase or decrease.

Small unilamellar vesicles (SUVs) are made of one single phospholipid bilayer and are obtained by ultrasonication of the multilamellar vesicles (MLVS) obtained by hydration of a phospholipid dry lipid film. They are known to be thermodynamically unstable at room temperature and spontaneously to fuse into multilamellar vesicles when stored in aqueous solutions (Reference 1). Although it has been reported that MLVs can be stored indefinitely at 4° C. without physical alteration (Reference 1), the problem of the encapsulated drug stability still has to be addressed.

When the encapsulated drug is hydrophobic and strongly encapsulated within the phospholipid bilayers SUVs can be prepared by freeze-drying (e.g. containing amphotericin B; Reference 2). This document, WO87/101933, describes a dehydrated liposome/amphotericin B composition which can be reconstituted with an aqueous medium, the composition being prepared by dehydrating a suspension of unilamellar vesicles in the presence of a membrane stabilizing agent which is a monosaccharide or a disaccharide such as glucose, mannitol, trehalose, sucrose or lactose. The mass ratio of trehalose/phospholipid is considered to be the most important unique factor for successful freeze drying.

The freeze drying of the liposomal encapsulated hydrophilic drugs is hazardous (References 3, 4 and 5), whilst the freeze drying of liposomal encapsulated amphiphilic drugs has not previously been described or contemplated.

Amphiphilic compounds are molecules which possess both a hydrophilic and a hydrophobic part. For example, phospholipids are amphiphilic compounds which comprise two hydrophobic fatty acid chains and a hydrophilic phosphocholine group. Amphiphilic compounds may be represented by uncharged hydrophobic and ionic hydrophilic species whose proportions depend upon the pH. The pK of such compounds is defined as the pH at which equal concentrations of both the uncharged and charged forms of the molecule are found.

Pharmaceutical compositions comprising bupivacaine, which is an amphiphilic compound, encapsulated in liposomes are described in U.S. Pat. No. 5,244,678 (Reference 6). The compositions which are described are in an injectable form and no teaching is provided in the specification of compositions in any other form. The encapsulation of bupivacaine in the liposomes is advantageous in that it leads to a superior anaesthetic action as compared to the non-encapsulated drug, to a longer lasting action at equal dosages and to the possibility of reducing the doses to achieve the same or a similar effect. It would be advantageous if the compositions comprising bupivacaine encapsulated in liposomes could be freeze dried in order that the composition could be prepared in bulk, readily stored and transported, and reconstituted as required ready for use.

GB-A-2256139 discloses liposome preparations containing terbinafine which are prepared using from 2 to 10% of certain cryoprotectants before the final lyophilisation.

WO87/01933 discloses a dehydrated liposome/amphotericin B composition which is prepared by forming a suspension of amphotericin B liposomes in aqueous solution containing at least 0.5 w/v of a membrane stabilizing agent, such as trehalose. Amphotericin B is a lipophilic drug.

We have now developed a process for freeze drying multilamellar vesicles (MLVS) which encapsulate an amphiphilic drug, such as bupivacaine, and which may be stored in the freeze dried form without significant modification of the vesicle size range, morphology and drug encapsulation ratio.

Accordingly, the present invention provides a process for the preparation of freeze dried liposome encapsulated amphiphilic drug compositions, which process comprises preparing a liposomal suspension of multilamellar vesicles (MLVs) which encapsulate an amphiphilic drug composition, adding sorbitol as a membrane stabilizing agent to the liposomal suspension in an amount of up to 1% wt/volume of the suspension agent and lyophilising of the suspension.

The lyophilisation of the liposomal suspension is preferably carried out by cooling the suspension to a temperature of about −25° C., preferably by direct immersion in denatured ethanol at −25° C.

The sorbitol is added to the suspension as the membrane stabilizing agent in an amount of up to 1% wt/volume of the suspension. The molar ratio of sorbitol to the phospholipid used in the formation of the liposomal suspension is preferably 8 or less.

The liposomal suspension of the multilamellar vesicles is preferably prepared by encapsulation of the amphiphilic drug in a phospholipid, optionally in combination with a sterol component. The molar ratio of the phospholipid to the sterol component is preferably in the range of from 4:0 to 4:4, more preferably about 4:3. The phospholipid is preferably phosphatidyl choline (PC) or dipalmitoylphosphatidyl choline (PPPC). The sterol component is preferably cholesterol.

The amphiphilic drug which is encapsulated in the liposomes which are freeze dried in accordance with the present invention may be a local anaesthetic, for example bupivacaine, ropivacaine, prilocaine, mepivacaine, tetrocaine or etidocaine, or a narcotic analgesic, for example morphine, fentanyl, alfentanil or sulfentanil.

The amphiphilic drug composition is generally encapsulated in the liposomes in an amount of from 1.25 to 10 mg/ml, preferably in an amount of from 5 to 10 mg/ml.

Techniques for the preparation of liposomal encapsulated drug compositions are generally known in the art and are described for example in Betageri et al. (Reference 1). They are obtained by dissolving phospholipid(s), cholesterol and a drug in hydrophilic form in an organic solvent, chloroform or dichloromethane. The organic solvent is evaporated under nitrogen atmosphere and the resulting lipid film is dried under vacuum. The dry lipid film is then hydrated with an aqueous medium, buffered or unbuffered, which may contain a hydrosoluble compound. The film is submitted to mild agitation and MLVs in aqueous suspension are obtained. As mentioned above, SUVs may be obtained by ultrasonication of MLV suspensions at 0° C. and under nitrogen.

The liposomal suspensions are generally formed as suspensions of MLV's in a phosphate buffer at a pH of about 8.1.

The present invention also includes within its scope a freeze dried encapsulated amphiphilic drug composition which has been prepared by the process of the invention.

The freeze dried composition of the present invention, upon rehydration, forms a suspension of MLV's which substantially maintains a) its native size distribution;

b) its drug/lipid ratio; and c) the morphology of the vesicles.

These advantages are not obtained if sorbitol is used as a membrane stabilizing agent in the freeze drying of SUV's, and is only obtained if other membrane stabilizing agents such as trehalose or glucose at concentrations higher than 1% are used as membrane stabilizing agents in the freeze drying of MLV's.

The present invention will be further described with reference to the following examples.

EXAMPLE 1

Bupivacaine was encapsulated in MLVs prepared from egg phosphatidyl choline (EPC) and cholesterol (Ch) (ratio 4:3) according to the following method. A preliposomal lipid film was obtained by drying under nitrogen atmosphere a mixture of EPC (14.4 mg=18.3 $\mu$moles), 5.6 mg cholesterol (13.7 $\mu$moles) and 5 mg (17.3 $\mu$moles) apolar hydrophobic bupivacine in an organic solvent such as dichloromethane or chloroform.

A liposomal suspension of the MLVs encapsulating the bupivacaine was prepared by hydrating the dry lipid film with 1 ml isotonic phosphate buffer (PBs) pH 8.1, followed by smooth shaking of the suspension during formulation.

Sorbitol was added to the suspension in an amount of 1% wt/volume, at a molar ratio of sorbitol to phospholipid of 3:1.

The liposomal suspension was then freeze dried at $-25°$ C. by direct immersion in denatured ethanol. The association of bupivacaine (encapsulation efficiency) with 1 ml of the liposomal suspension before freeze drying was 82.8% ± 1.5%. After freeze drying the encapsulation efficiency was 82.5%.

EXAMPLE 2

The procedure of Example 1 was used to provide a scaled-up liposome-bupivacaine sample as used in clinical trials (Reference 8 and 9), i.e. a 11–20 ml sterile and pyrogen-free suspension of liposome encapsulated 0.5% bupivacaine indicated that not only the encapsulation efficiency (E.E.), but also the molar ratio of bupivacaine to phospholipid were maintained on freeze drying and reconstitution, as detailed in the following Table 1.

TABLE 1

| Solution | E. E. (%) | MLV-BP (mg/ml) | EPC/Ch (mg/ml) | Drug/Lipid Molar Ratio |
|---|---|---|---|---|
| Native MLV-BP (n = 10) | 88.9 ± 2.3 | 3.8 ± 0.3 | 15.4 ± 0.3 | 0.673 |
| Lyophilizate 1 | 88.1 | 3.8 | 15.4 | 0.673 |
| Lyophilizate 2 | 87 | 3.8 | 15.4 | 0.673 |

EXAMPLE 3

Sizing of the MLVs of Example 2 was studied by laser light scattering (Reference 7) plotting the logarithm of vesicle diameters against the percentage of the population.

EXAMPLE 4

Figure 1:
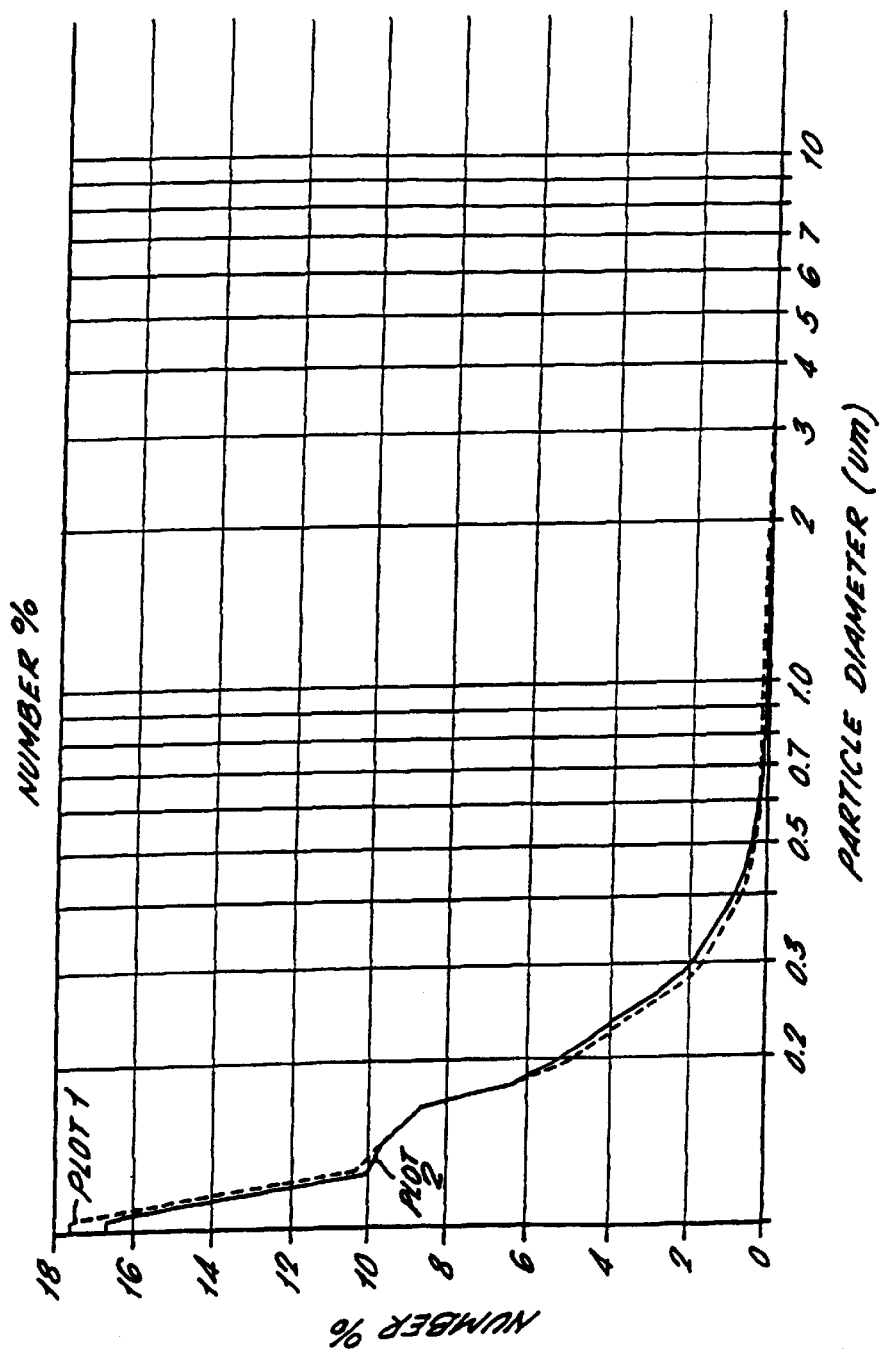
FIG. 1 illustrates the similarity of liposome size distribution as a function of the percentage of the liposome population before freeze drying (Plot 1) and after freeze drying and with subsequent rehydration (Plot 2).

The following Table 2 compares the size percentiles in empty liposomes of EPC:Ch (4:3 ratio), in a liposome-associated bupivacaine (0.5%) composition and in 4 lyophilizates of 11 ml samples of this composition. While the association of bupivacaine with MLVs slightly increased the vesicle size range, the addition of sorbitol and the freeze-drying procedure of the MLV-BP 0.5% liposomes did not significantly modify the size distribution of preparations 1 to 2 when rehydrated.

This result was unexpected since in all freeze drying assays of unilamellar vesicles variations of 10 to 30% of the size distribution was found (Reference). When freeze drying of SUVs was carried out using sorbitol at a concentration of 10 mg/ml, a more than ten fold increase of size was observed on rehydration (Reference 2).

TABLE 2

Cumulative size percentiles from liposome-associated bupivacaine (0.5%) composition and of 4 rehydrated 11 ml samples of this composition after sonication for 1 minute for Coulterometry.

| Conditions | 10% | 25% | 50% | 755 | 90% |
|---|---|---|---|---|---|
| Empty MLV | 0.263 | 0.187 | 0.142 | 0.115 | 0.105 |
| MLV-BP | 0.27 | 0.194 | 0.145 | 0.116 | 0.106 |
| MLV-BP + Sorb. | 0.272 | 0.195 | 0.145 | 0.116 | 0.106 |
| Lyoph. 1 | 0.243 | 0.182 | 0.14 | 0.114 | 0.105 |
| Lyoph. 2 | 0.262 | 0.19 | 0.143 | 0.116 | 0.106 |
| Lyoph. 3 | 0.25 | 0.185 | 0.141 | 0.115 | 0.105 |
| Lyoph. 4 | 0.243 | 0.182 | 0.14 | 0.114 | 0.105 |

REFERENCES

1. Betageri G V, Jenkins S A, Parsons D L. *Liposome Drug Delivery Systems*. Lancaster: Technomic Publishing Co (1993).

2. Abra R, Szoka F C. Stabilized liposome/amphotericin composition and method. PCT/US/01881; WO 87/01933 (1987).

3. Crowe J H, Crowe L M. Biochimica Biophysica Acta 939:327–334 (1988).

4. Crommelin D J A, Van Bommel E M G. Pharmaceutical Research: 159–163 (1984).

5. Schmidt P G. Method of making liposomes with improved stability during drying. Patent WO90/03795 (1988).

6. U.S. Pat. No. 5,244,678

7. Hauser P. Phospholipid vesicles. *Phospholipids Handbook*. Edited by Cevc G. New York: Marcel Dekker, 603–637 (1993).

8. Boogaerts J G, Lafont N D, Declercq A G, Luo H C, Gravet E T, Bianchi J A, Legros F J, Epidural administration of liposome-associated bupivacaine for the management of postsurgical pain: A first study, Journal of Clinical Anethesia 6:315–320 (1994).

9. Boogaerts J G, Lafont N D, Legros F J, Lipsome-associated bupivacaine in postsurgical analgesia: Dose-Response relationship. Anesthesiology 81:A995 (1964).

What is claimed is:

1. A process for the preparation of freeze dried liposome encapsulated amphiphilic drug compositions, which process comprises preparing a liposomal suspension of multilamellar vesicles (MLVs) which encapsulate an amphiphilic drug composition, adding sorbitol as a membrane stabilizing agent to the liposomal suspension in an amount of up to 1% wt/volume of the suspension agent and lyophilising of the suspension.

2. A process as claimed in claim 1 wherein the lyophilisation is carried out by cooling of the suspension to −25° C.

3. A process as claimed in claim 1 preceding claims wherein the liposomal suspension is prepared from a phospholipid optionally in combination with a sterol.

4. A process as claimed in claim 3 wherein the molar ratio of phospholipid: sterol is in the range of 4:0 to 4:4.

5. A process as claimed in claim 3 wherein the phospholipid is phosphatidyl choline or dipalmitoylphosphatidyl choline.

6. A process as claimed in claim 3 wherein the sterol is cholesterol.

7. A process as claimed in claim 1 wherein the amphiphilic drug is bupivacaine, ropivacaine, prilocaine, mepivacaine, tetrocaine, etidocaine, morphine, fentanyl, alfentanil or sulfentanil.

8. A process as claimed in claim 1 wherein the molar ratio of sorbitol to phospholipid is 8 or less.

9. A freeze dried liposome encapsulated amphiphilic drug composition whenever prepared by a process as claimed in claim 1.

10. A freeze dried liposome encapsulated amphiphilic drug composition as claimed in claim 9 which upon rehydration forms a suspension of liposomes which maintains the size distribution and morphology of the original liposomal suspension before freeze drying.

11. A freeze dried liposome encapsulated amphiphilic drug composition as claimed in claim 9 which upon rehydration forms a suspension of liposomes which maintains the drug to lipid ratio of the original liposomal suspension before freeze drying.

* * * * *